(12) United States Patent
Simon et al.

(10) Patent No.: US 6,292,699 B1
(45) Date of Patent: Sep. 18, 2001

(54) DIRECT CURRENT STIMULATION OF SPINAL INTERBODY FIXATION DEVICE

(75) Inventors: Bruce J. Simon, Mountain Lakes; Jeffrey D. Schwardt, Morristown, both of NJ (US)

(73) Assignee: Electro-Biology, Inc., Parsippany, NJ (US)

( * ) Notice: Subject to any disclaimer, the term of this patent is extended or adjusted under 35 U.S.C. 154(b) by 0 days.

(21) Appl. No.: 09/240,111

(22) Filed: Jan. 29, 1999

(51) Int. Cl.$^7$ ...................................................... A61N 1/20
(52) U.S. Cl. ................................................. 607/51; 607/75
(58) Field of Search .................................. 607/51, 75, 2, 607/52, 50; 623/17, 16, 17.11, 16.11

(56) References Cited

U.S. PATENT DOCUMENTS

| | | | |
|---|---|---|---|
| 3,783,880 | * 1/1974 | Kraus ...................................... | 607/51 |
| 3,918,440 | * 11/1975 | Kraus ...................................... | 607/51 |
| 4,175,565 | 11/1979 | Chiarenza et al. ....................... | 433/32 |
| 4,306,564 | 12/1981 | Kraus ...................................... | 128/419 |
| 4,421,115 | 12/1983 | Kraus ...................................... | 128/419 |
| 4,430,999 | * 2/1984 | Brighton et al. ......................... | 607/51 |
| 4,501,269 | 2/1985 | Bagby ...................................... | 128/92 |
| 4,506,674 | * 3/1985 | Brighton et al. ......................... | 607/51 |
| 4,558,701 | 12/1985 | Spalten ................................... | 128/419 |
| 4,781,591 | 11/1988 | Allen ...................................... | 433/174 |
| 4,889,111 | * 12/1989 | Ben-Dov ................................. | 607/51 |
| 5,015,247 | 5/1991 | Michelson .............................. | 606/61 |
| 5,030,236 | 7/1991 | Dean ....................................... | 623/16 |
| 5,304,210 | 4/1994 | Crook ...................................... | 607/51 |
| 5,489,307 | 2/1996 | Kuslich et al. .......................... | 623/17 |
| 5,489,308 | 2/1996 | Kuslich et al. .......................... | 623/17 |
| 5,738,521 | 4/1998 | Dugot ..................................... | 433/173 |

FOREIGN PATENT DOCUMENTS

WO 95/32673    12/1995    (WO) .

OTHER PUBLICATIONS

Spadaro, Joseph A., "Bioelectrochemistry Studies of Implantable Bone Stimulation Electrodes," *Bioelectrochemistry and Bioenergetics* 5, pp. 232–258 (1978).

Salman, N.N. et al., "The Effect of Direct Electrical Current Stimulation on the Bone/Porous Metallic Implant Interface," Apr. 28, 1980.

Brighton, Carl T. et al., "Electrically Induced Osteogenesis: Relationship between Charge, Current Density, and the Amount of Bone Formed: Introduction of a New Cathode Concept," in *Clinical Orthopaedics and Related Research*, pp. 122–132, 1981.

Brighton, C.T., "Present and Future of Electrically Induced Osteogenesis," in *Clinical Trends in Orthopaedics*, Ed. L.R. Straub et al., pp. 1–15, 1981.

Colella, S.M. et al, "Fixation of Porous Titanium Implants in Cortical Bone Enhanced by Electrical Stimulation," *Journal of Biomedical Materials Research*, vol. 15, pp. 37–46, 1981.

Black, J. et al., "The Role of Electrode Material and Current Density in Electrical Stimulation of Osteogenesis," Paper presented at $2^{nd}$ Annual BRAGS, Oxford, U.K., Sep. 20–22, 1982.

(List continued on next page.)

Primary Examiner—Kennedy Schaetzle
(74) Attorney, Agent, or Firm—Woodard, Emhardt, Naughton, Moriarty & McNett

(57) ABSTRACT

A spinal fusion stimulator comprising an interbody fusion cage or other interbody fixation device adapted to be implanted in the intervertebral disc space of a patient's spine, the interbody fusion cage in the preferred embodiment having a hollow body with internal and external conductive surfaces. The stimulator includes a constant current generator connected to the interbody fusion cage and set to provide a DC current effective to produce a surface current density of at least 1 $\mu A/cm^2$ in the interbody fusion cage when implanted.

13 Claims, 1 Drawing Sheet

OTHER PUBLICATIONS

Spadaro, J.A. et al., "Electrically Enhanced Osteogenesis at Various Metal Cathodes," *Journal of Biomedical Materials Research*, vol. 16, No. 6, pp. 861–873, 1982.

Buch, F. et al., "The Bone Growth Chamber for Qunatification of Electrically Induced Osteogenesis," *Journal of Orthopaedic Research*, vol. 4, pp. 194–203, 1986.

Meril, Allen J., "Direct Current Stimulation of Allograft in Anterior and Posterior Lumbar Interbody Fusions," *Spine*, vol. 19, No. 21, pp. 2393–2398, 1994.

Black Jonathan, et al., "Mechanisms of Stimulation of Osteogenesis by Direct Current," in *Electrical Properties of Bone and Cartilage—Experimental Effects and Clinical Application*, Brighton, Black and Pollack, ed., Grune and Stratton, New York, pp. 215–224, 1979.

"Anterior Surgical Technique—BAK™ Lumbar Interbody Fusion System," Spine–Tech, Inc. manual, 1996.

Meril, Allen, "Surgical Technique for the Use of Direct Current Stimulation with Titanium Interbody Cages," Abstract of presentation at a workshop, part of 8$^{th}$ Meeting of the European Spine Society, Kos–Hellas, Greece, Sep. 1997 (1 page).

Meril, Allen J. "Surgical Technique for the Use of Direct Current (DC) Stimulation with Titanium Interbody Cages," handout from the 8$^{th}$ Meeting of the European Spine Society, Kos–Hellas, Greece, Sep. 1997 (5 pages).

"SpF Implantable Spinal Fusion Stimulators, Procedures for Surgical Use," EBI brochure, Dec. 1997.

"Implantable Direct Current Stimulation of Spinal Fusion," EBI Medical Systems, Inc. brochure, May 1998.

\* cited by examiner

DIRECT CURRENT STIMULATION OF SPINAL INTERBODY FIXATION DEVICE

BACKGROUND OF THE INVENTION

This application relates generally to spinal fusion devices and methods and, more particularly, to spinal fusion devices and methods employing direct current (DC) bone growth stimulation as an adjunct to interbody fusion.

Approximately 100,000 lumbar spine fusion surgeries are performed annually in the U.S. on patients with lower back pain due to degenerative disc disease or spondylolisthesis. Adjacent vertebrae are fused together in such surgical procedures, thereby eliminating motion among the spine levels and significantly reducing lower back pain in most patients. Known spinal fusion methods include posterolateral fusion, also known as inter-transverse process fusion because it involves fusion of the transverse processes of adjacent vertebrae, and interbody fusion, which involves fusion of the bodies of adjacent vertebrae. Traditional interbody fusion involves insertion of autograft or allograft (bone graft from the patient's own body or from another body, respectively) into the intervertebral disc space as a spacer.

Interbody fusion is gaining popularity as an alternative to posterolateral fusion. The introduction of threaded titanium interbody fusion cages has made this technique simpler and more common among orthopedists and neurosurgeons. Such a cage is typically a rigid, hollow cylinder with a pattern of holes through its sidewall to allow bone growth into and through the cage. The cage is typically filled with morselized bone to facilitate fusion by bone growth through the cage, which thereby promotes interbody fusion. A number of interbody fusion devices and techniques have been proposed, as exemplified by those described in the following patents:

| Patent No. | Inventor | Issue Date |
| --- | --- | --- |
| 4,501,269 | Bagby | February 26, 1985 |
| 4,961,740 | Ray | October 9, 1990 |
| 5,015,247 | Michelson | May 14, 1991 |
| 5,489,307 | Kuslich et al. | February 6, 1996 |
| 5,489,308 | Kuslich et al. | February 6, 1996 |

Fusion success rates greater than 85% at 1–2 year follow-ups have been reported for titanium interbody fusion cages in one-level fusions, whereas the success rates for such cages in two-level fusions have been reported to be approximately 70–80%. Fusion success rates as low as 70% present a serious and expensive problem, since a large portion of patients require revision surgery, which is costly, painful, and disabling. One proposed solution to the problem is to pack interbody fusion cages with synthetic bone growth factors, particularly bone morphogenic proteins, which exhibit the ability to induce bone and/or cartilage formation. There is a safety concern over the potential formation of ectopic bone on or near the spinal cord with the use of potent growth factor products. It is also believed that bone growth factors remain at the fusion site for only hours or at most a few days before diffusing away.

Implantable direct current bone growth stimulation has been established as a useful adjunct for posterolateral fusion as well as for the traditional type of interbody fusion involving bone graft alone as the interbody spacer. Spinal fusion stimulators with titanium cathodes are available from Electro-Biology, Inc., the assignee of the present invention, and have been employed with the titanium cathodes placed in contact with bone graft material and the decorticated spine to deliver direct current to the fusion site. A small direct current (typically 20 or 40 $\mu$A divided among multiple cathodes) is delivered constantly for six months to enhance bone fusion. However, physicians are cautioned not to allow any metallic part of the stimulator to contact any metal internal fixation device. Bone graft is packed in and around the cathodes to form a fusion mass in which the cathodes are completely embedded.

In spite of all known adjuncts for interbody fusion, there remains a need for devices and methods for speeding interbody fusion and increasing fusion success rates.

SUMMARY OF THE INVENTION

The present invention meets this need and provides significant advantages over prior art devices and methods with a spinal fusion stimulator adapted to supply a constant DC current directly to an interbody fixation device adapted to be implanted in the intervertebral disc space of a patient's spine. The interbody fixation device functions as the electronegative cathode in addition to providing immediate stabilization and weight-bearing capability. DC current is supplied at a current level effective to produce a surface current density in said interbody fixation device that is effective to enhance osteogenesis. According to one aspect of this invention, a current density of at least 1 $\mu$A/cm$^2$ is produced in the interbody fixation device when implanted.

Another aspect of the invention is a method of stimulating spinal fusion that includes implanting an interbody fixation device in the intervertebral disc space of a patient's spine, and supplying a constant DC current to the interbody fixation device at a level based on the exposed electrically conductive surface area of the interbody fixation device and a predetermined desired surface current density.

A general object of the present invention is to provide an improved method and apparatus for promoting osteogenesis in interbody fusion.

Another object of the present invention is to employ direct current bone growth stimulation with a direct connection to an interbody fixation device with sufficient surface current density to significantly improve the efficacy of the interbody fusion.

These and other objects and advantages of the present invention will be more apparent upon reading the following detailed description in conjunction with the accompanying drawings.

DETAILED DESCRIPTION OF THE PREFERRED EMBODIMENT

Figure 1:
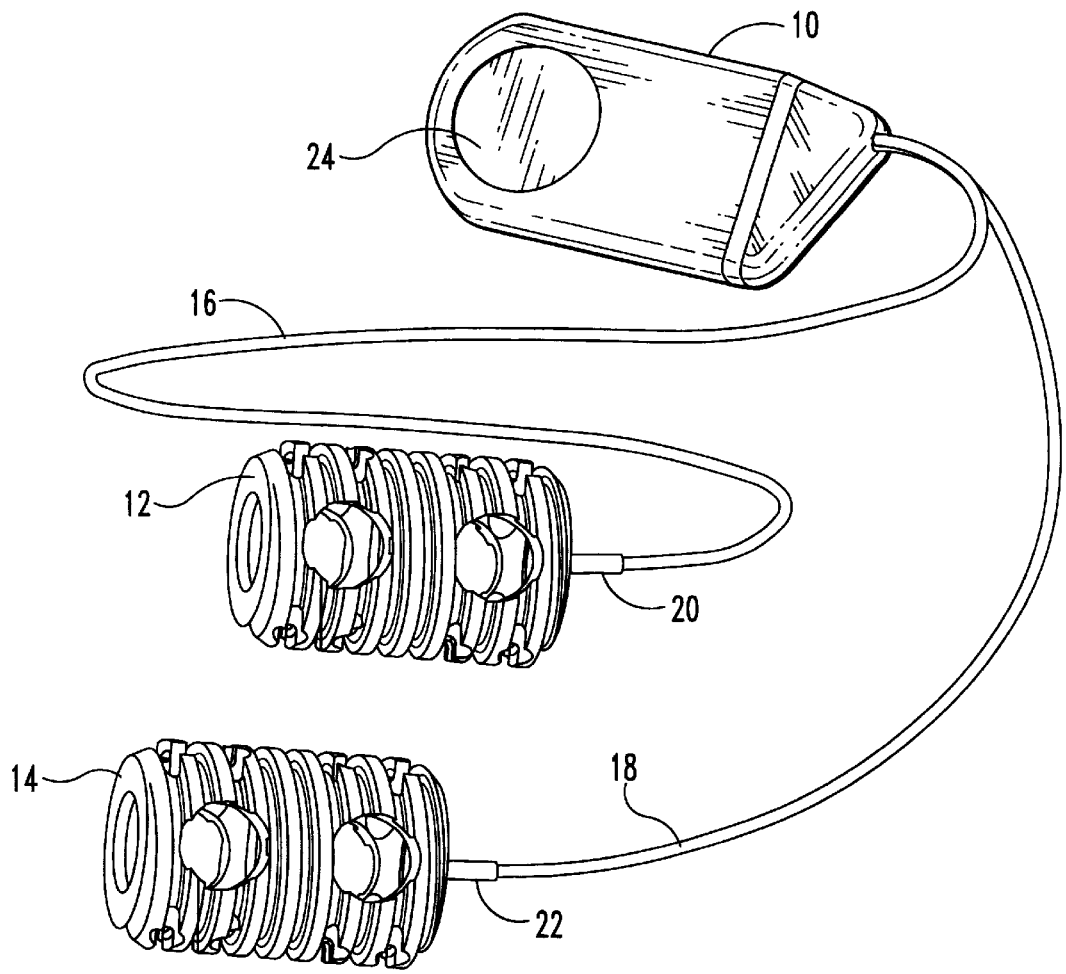
FIG. 1 is a perspective view of the preferred embodiment of a spinal fusion stimulator with interbody fusion cages according to the present invention.

For the purpose of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

With reference to FIG. 1, an implantable DC generator 10 is preferably connected to a pair of titanium interbody fusion cages 12 and 14 via respective insulated lead wires 16 and 18 and connectors 20 and 22. DC generator 10 may be of the type commercially available from Electro-Biology, Inc., the assignee of the present invention, in its SPF® line of spinal fusion stimulators, except modified to provide a surface area current density appropriate to the interbody fusion cages as will be described. DC generator 10 includes a platinum or iridium oxide surface 24 that serves as an electropositive anode. Lead wires 16 and 18 are conventional lead wires of the type used with EBI SPF® fusion stimulators. Connectors 20 and 22 are designed to be suitable for attachment to any of several titanium interbody fusion cage devices, including, for example, the BAK™ interbody fusion cage available from Spine-Tech, Inc., the Ray cage available from Surgical Dynamics and the Novus threaded fusion cage (TFC) available from Sofamor Danek. Interbody fusion cages appropriate for the present invention are preferably made of either pure titanium or 6Al—4Va titanium alloy, although other suitable biocompatible electrode materials may also be used such as tantalum, platinum and others disclosed in U.S. Pat. No. 5,458,627 to Baranowski et al., which patent is hereby incorporated by reference. If desired, an interbody fusion cage may be preoperatively prepared for use with the present invention by permanent attachment of a connection terminal thereto, e.g., by welding a stud thereto for subsequent connection to a connector on the end of one of the lead wires from the signal generator. Alternatively, an attachable connector, with spring or screw-clamp mechanism, would create a conductive connection to a fixation device. Other types of fixation devices are also contemplated, as will be described herein.

Figure 2:
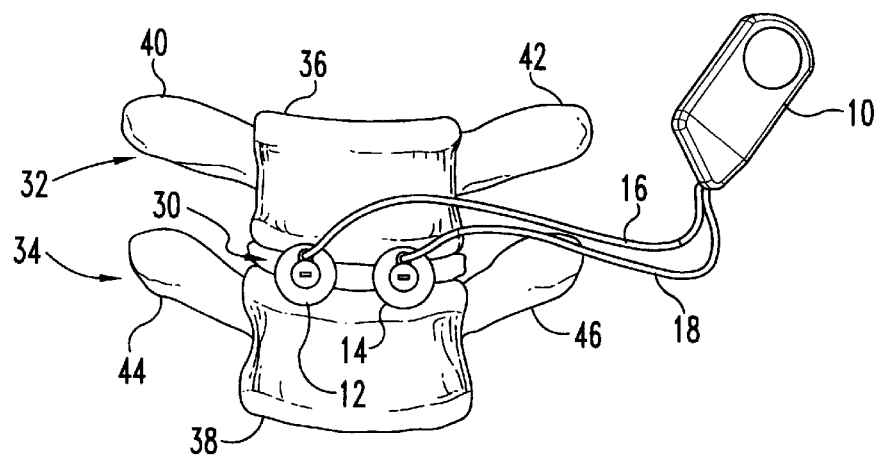
FIG. 2 is an anterior view of a spinal segment with the interbody fusion cages of FIG. 1 implanted therein.

The present invention is suitable for interbody fusion from an anterior approach or a posterior approach. For purposes of illustration, however, an anterior lumbar interbody fusion employing the principles of the present invention is shown in FIG. 2, wherein it can be seen that fusion cages 12 and 14 are inserted side-by-side in the intervertebral space 30 between two adjacent vertebrae 32 and 34 having respective vertebral bodies 36 and 38 and pairs of transverse processes 40 and 42 and 44 and 46. According to the preferred method of implantation, the interbody fusion cages are first implanted into respective evacuated disc spaces and then the two insulated lead wires are attached thereto. The site is prepared and the fusion cages are selected and packed with graft material and then inserted into the disc spaces in a conventional manner, and the DC generator is implanted at an appropriate subcutaneous or intramuscular site, e.g., on the psoas muscle in the case of an anterior lumbar interbody fusion.

According to the present invention, the interbody fusion cages function both as weight-bearing mechanical fixation devices and as electronegative bone stimulation electrodes. Electrification of titanium interbody fusion cages by direct delivery of electric current to the cages can speed the rate of bony incorporation of cages and raise success rates, especially for high-risk patients or in fusions involving two or more levels of the lumbar spine. Direct current technology is relatively cost effective and therefore more available to patients. The treatment is highly localized, which eliminates the safety issues related to ossification of the spinal cord. Direct current will have a very strong effect inside the cage, where bony fusion is most important.

Important to the osteogenic efficacy of an electrically stimulated interbody fusion cage is the level of current applied to the cage. There is believed to be a therapeutic window or range of surface current densities within which the current density is high enough to be efficacious, i.e., to promote bone growth, but not so high as to be toxic or cause necrosis. It is presently believed that this therapeutic window extends from a current density not less than 1 $\mu A/cm^2$ to a current density of approximately 150 $\mu A/cm^2$. While current densities outside this range may be efficacious to some degree, current densities within this range are believed to provide significantly better results.

DC generator 10 is preferably designed to be adjustable so as to have the capability of providing sufficient current to generate current densities in the therapeutic window for various sizes of interbody fusion cages. For example, with a BAK™ cage of a nominal implant size of 11 mm (11 mm in diameter and 20 mm in length), the total exposed electrically conductive surface area of the cage is approximately 21.3 $cm^2$, and the corresponding current required to be supplied to the cage to provide a current density of 1 $\mu A/cm^2$ is approximately 20 $\mu A$. Experimental studies have demonstrated enhanced bony ingrowth in a BAK™ cage of this size with a current level of 40 $\mu A$, corresponding to a current density of approximately 1.9 $\mu A/cm^2$, and have demonstrated excellent efficacy with a higher current level of 100 $\mu A$, corresponding to a current density of approximately 4.7 $\mu A/cm^2$. Such results were obtained after four months of direct current stimulation of the fusion cage in sheep lumbar fusions. Alternatively, the DC generator may be set to deliver current at a fixed level of, for example, 100 $\mu A$ to a predetermined range of sizes of fusion cages for which the fixed current level is effective to produce a surface current density in the therapeutic window. Electric current according to the present invention may be delivered for a period of anywhere from one to twelve months, although treatment for a period of six months is most preferred.

As alluded to above, interbody fixation devices other than cylindrical fusion cages are contemplated, including cages having a square or other cross-section, and other devices that span the intervertebral space.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed:

1. A method of stimulating spinal fusion, comprising:

implanting an interbody fixation device in the intervertebral disc space of a patient's spine; and supplying a constant DC current to said interbody fixation device at a level based on the exposed electrically conductive surface area of said interbody fixation device and a predetermined desired surface current density.

2. The method of claim 1, wherein said constant DC current is supplied at a current level effective to produce a surface current density in the range of approximately 1–150 $\mu A/cm^2$.

3. The method of claim 2, wherein said interbody fixation device has a total exposed conductive surface area of at least 20 $cm^2$.

4. The method of claim 3, wherein said constant DC current is supplied at a current level effective to produce a surface current density in the range of approximately 1–40 $\mu A/cm^2$.

5. The method of claim 4, wherein said constant DC current is supplied for a treatment period in the range of 1–12 months.

6. The method of claim 1, wherein said constant DC current is greater than 20 $\mu A$.

7. The method of claim 6, wherein said constant DC current is approximately 100 $\mu A$ and wherein said surface current density is approximately 5 $\mu A/cm^2$.

8. The method of claim 1, wherein said surface current density is approximately 5 $\mu A/cm^2$.

9. The method of claim 1, wherein said constant DC current is supplied at a current level effective to produce a surface current density in the range of approximately 1–40 $\mu A/cm^2$.

10. The method of claim 9, wherein said constant DC current is supplied for a treatment period in the range of 1–12 months.

11. A method of stimulating spinal fusion, comprising:

implanting an interbody fixation device in the intervertebral disc space of a patient's spine; and supplying a constant DC current to said interbody fixation device at a level set for a predetermined range of sizes of said interbody fixation device to produce a surface current density in a range between 1 and 40 $\mu A/cm^2$.

12. The method of claim 11, wherein said range is approximately 2–20 $\mu A/cm^2$.

13. The method of claim 12, wherein said range is approximately 2–5 $\mu A/cm^2$.

* * * * *